United States Patent
Martens

(10) Patent No.: US 8,498,709 B2
(45) Date of Patent: Jul. 30, 2013

(54) PLANNING SYSTEM FOR NEUROSTIMULATION THERAPY

(75) Inventor: Hubert Cecile Francois Martens, Eindhoven (NL)

(73) Assignee: Sapiens Steering Brain Stimulation B.V., Eindhoven (NL)

( * ) Notice: Subject to any disclaimer, the term of this patent is extended or adjusted under 35 U.S.C. 154(b) by 3 days.

(21) Appl. No.: 13/285,136

(22) Filed: Oct. 31, 2011

(65) Prior Publication Data
US 2012/0109599 A1    May 3, 2012

(30) Foreign Application Priority Data
Oct. 29, 2010    (EP) .................................. 10189497

(51) Int. Cl.
*A61N 1/18*    (2006.01)

(52) U.S. Cl.
USPC .......................................................... 607/45

(58) Field of Classification Search
USPC .......................................................... 607/45
See application file for complete search history.

(56) References Cited

U.S. PATENT DOCUMENTS

| | | | |
|---|---|---|---|
| 7,442,183 B2 | 10/2008 | Baudino et al. | |
| 2008/0215125 A1 | 9/2008 | Farah et al. | |
| 2009/0259274 A1* | 10/2009 | Simon et al. | 607/40 |
| 2009/0287271 A1 | 11/2009 | Blum et al. | |
| 2010/0030298 A1 | 2/2010 | Martens et al. | |
| 2010/0268298 A1* | 10/2010 | Moffitt et al. | 607/45 |

FOREIGN PATENT DOCUMENTS

| | | |
|---|---|---|
| WO | 2004096018 A2 | 11/2004 |
| WO | 2006034305 A2 | 3/2006 |

OTHER PUBLICATIONS

International Search Report dated Dec. 21, 2012 for international patent application No. PCT/EP2011/069104.

* cited by examiner

*Primary Examiner* — Carl H Layno
*Assistant Examiner* — Paula J Stice
(74) *Attorney, Agent, or Firm* — Morgan, Lewis & Bockius LLP

(57) ABSTRACT

A system for planning implantation of a neurostimulation probe is provided. The system comprises an input for receiving anatomical data comprising information regarding a position and an orientation of at least one fiber bundle in a target region, an input for receiving therapeutic information comprising information regarding a stimulation preferability of the at least one fiber bundle, an optimization module for based on the position, the orientation and the stimulation preferability of the at least one fiber bundle calculating at least one optimal position and at least one optimal orientation for implantation of the neurostimulation probe at which optimal position and orientation the probe is capable of generating an electric field gradient substantially parallel to at least one fiber bundle with a high stimulation preferability and/or substantially perpendicular to at least one fiber bundle with a low stimulation preferability and an output for providing the optimal position and orientation.

7 Claims, 2 Drawing Sheets

PLANNING SYSTEM FOR NEUROSTIMULATION THERAPY

CROSS-REFERENCE TO RELATED APPLICATIONS

This application claims the benefit of European Patent Application No. 10 189 497.0 filed Oct. 29, 2010, incorporated by reference herein in its entirety.

FIELD OF THE INVENTION

This invention relates to a system for planning implantation of a neurostimulation probe, the system comprising an input for receiving anatomical data comprising information regarding a position of at least one fiber bundle in a target region, an input for receiving therapeutic information comprising information regarding a stimulation preferability of the at least one fiber bundle, an optimization module for based on the position and the stimulation preferability of the at least one fiber bundle calculating an optimal position for implantation of the neurostimulation probe at which the probe is positioned to enable stimulation of at least one fiber bundle with a high stimulation preferability and an output for providing the optimal position.

This invention further relates to a method and a computer program product for planning implantation of a neurostimulation probe.

BACKGROUND OF THE INVENTION

Systems for providing neurostimulation via an implanted probe are used for treatment of disorders such as chronic pain, Parkinson's disease, tremor and dystonia. Neurostimulation is used for stimulating neural tissue in the brain, the spinal cord and peripheral nerves. In the following, neurostimulation of brain tissue will be discussed. However, the system and method according to the invention can also be used for neurostimulation of, e.g., the spinal cord and peripheral nerves. The probe is surgically implanted in the brain, close to the brain tissue that is to be stimulated. When using neurostimulation it is important to stimulate the tissue that needs stimulation and to avoid stimulation of other nearby tissue. Correct placement of the probe thus is an important step in a successful neurostimulation treatment. In known systems for planning implantation of the probe, imaging techniques such as Magnetic Resonance Imaging (MRI) are used to visualize the target region. The surgeon tries to locate the structures that need stimulation and tries to define a surgical plan to implant the probe in the identified structure.

In a pending patent application of the same applicant as the present patent application, with application number EP10159853.0 (internal reference PH014693EP1) an example of a system for planning neurosurgical operations is described. The system described therein uses different imaging techniques to determine a surgical trajectory avoiding the critical neural structures. Said system could be useful for planning a trajectory for implanting a neurostimulation probe, but cannot be used for determining an optimal location for successful neurostimulation treatment.

A known way of trying to stimulate the correct tissue region is to implant a probe with a plurality of electrodes and to select only a subset of these electrodes so as to stimulate only specific tissue regions. This is, e.g., described in U.S. patent application US 2008/0215125. This U.S. application describes a probe with a plurality of electrodes which is implanted close to the region of interest. Electrical charges are supplied to a subset of these electrodes to selectively stimulate specific tissue regions. Also in U.S. Pat. No. 7,442,183 a subset of a plurality of electrodes is activated to steer an electrical field to the target region. In U.S. Pat. No. 7,442,183, it is noted that the selective activation of a subset of the electrodes makes the precise probe location relative to the target structure less critical.

Although the use of electrode arrays does enable steering 3D electric field distributions to specific tissue regions, the full range of 3D stimulation patterns that can be created is still dependent on the exact position and orientation of the probe. For optimal therapy delivery options and tuning flexibility thereof an optimal lead positioning should be arranged in the therapy planning phase.

OBJECT OF THE INVENTION

It is an object of the invention to provide a system for planning implantation of a neurostimulation probe, which system allows for a more accurate positioning of the probe in order to improve the neurostimulation treatment.

BRIEF SUMMARY OF THE INVENTION

According to a first aspect of the invention, this object is achieved by providing a system for planning implantation of a neurostimulation probe, the system comprising an input for receiving anatomical data comprising information regarding a position and an orientation of at least one fiber bundle in a target region, an input for receiving therapeutic information comprising information regarding a stimulation preferability of the at least one fiber bundle, an optimization module for based on the position, the orientation and the stimulation preferability of the at least one fiber bundle calculating at least one optimal position and at least one optimal orientation for implantation of the neurostimulation probe at which optimal position and orientation the probe is capable of generating an electric field gradient substantially parallel to at least one fiber bundle with a high stimulation preferability and/or substantially perpendicular to at least one fiber bundle with a low stimulation preferability and an output for providing the optimal position and orientation.

The planning system according to the invention does not only take into account the position of the target structure but also its orientation for planning the implantation of the neurostimulation probe. Especially for fiber bundles, the orientation of the electric stimulation field relative to the orientation of the fiber bundle is an important factor determining the effectiveness of the neurostimulation therapy. While the prior art planning systems only try to stimulate the brain at specific target positions, the planning systems according to the invention also takes into account the direction of the target fibers and the direction of the gradients of the electric stimulation fields that can be generated by the neurostimulation probe. It is to be noted that the planning system according to the invention may also be used for planning the implantation of two or more probes. However, in the following we will assume that only one probe is to be implanted.

It has been found that activation of certain fibers is most easily achieved when the electric field gradient is parallel or approximately parallel to the targeted fiber bundle. Selective non-activation of the fibers is most easily achieved with an electric field gradient that is perpendicular or approximately perpendicular to the non-targeted fiber bundle. Using state of the art imaging techniques, such as Diffusion Tensor Imaging (DTI), it is possible to identify individual fiber bundles and their positions and orientations. The optimization module uses this information to determine the optimal probe position and orientation. The planning system according to the invention thereby makes it possible to generate electric stimulation fields with field gradients that are (approximately) parallel to fiber bundles that should be stimulated and (approximately) perpendicular to fiber bundles that should not be stimulated.

The system according to the invention may comprise an imaging apparatus and may derive fiber bundle positions and orientations from images obtained by the imaging apparatus. Alternatively, the system may receive the image information regarding the fiber bundle positions and orientations from an external source or a brain atlas containing fiber orientations may be registered to anatomic images like MRI.

The system also receives information regarding the stimulation preferability of one or more fiber bundles. The stimulation preferability may, e.g., be provided as a simple list of fiber bundles that need stimulation for obtaining a desired therapeutic effect. Also a list of fiber bundles that should not be stimulated in order to avoid adverse side effects may be provided. The stimulation preferability is preferably expressed as a value indicating a level of desirability for a certain fiber bundle to be stimulated. The stimulation preferability may be obtained by a user selecting one or more fibers that should (or should not) be stimulated. For example, a pointing device such as a mouse or joystick may be used for highlighting important fiber bundles in a displayed image of the target region. The user may also be allowed to assign a level of stimulation preferability to the highlighted fiber bundles. Alternatively, the anatomical information may include information identifying the different fiber bundles and the therapeutic information may include information about what fiber bundles are to be stimulated. The system may then be arranged to select the fiber bundles that need stimulation.

The optimization module uses the gathered information (anatomical information with positions and orientations of fiber bundles and therapeutic information indicating stimulation preferabilities) to determine an optimal position and orientation for implantation of the probe. At the optimal position and orientation of the probe, the therapeutic effect of the stimulation may be maximized or the adverse side effects of the stimulation therapy may be minimized. In most cases the optimal position and orientation of the probe will provide a balance between maximizing expected positive effects and minimizing the expected adverse effects. Instead of one optimal position and orientation, the optimization module may also provide multiple optimal or close to optimal positions and orientations or a range of suitable positions and orientations.

If the probe to be implanted is a multi-electrode probe, the optimization module may take into account the possible 3D electrical field distributions that can be generated by the plurality of electrodes. Due to constraints on the distribution of stimulation electrodes (e.g. the geometry of the probe, limitation on the number of probes that can safely be implanted) not all 3D configurations of stimulation fields can be constructed. For example for axially shaped probes with multiple cylindrical electrodes it is easier to control field gradients parallel to the axis of the probe than to control perpendicular field gradients. For probes carrying (2D) electrode arrays on a cylindrical carrier body more field configurations become available. However, due to unavoidable geometric constraints for placement of the electrodes on the probe body, still only field gradients within certain limitations are possible. The optimization module in the system according to the invention may solve such problems by comparing the possible 3D orientations for the stimulation field to the positions and orientations of fiber bundles that should (or should not) be stimulated.

At the output, the planning system provides the optimal position and orientation for implantation of the probe. This information may, e.g., be provided by superimposing a graphical representation of the probe on an image of the target region.

According to a second aspect of the invention, a method of planning implantation of a neurostimulation probe is provided. The method comprises the steps of receiving anatomical data and therapeutic data, calculating at least one optimal position and at least one optimal orientation for implantation of the probe and providing the optimal position and orientation. The anatomical data comprises information regarding a position and an orientation of at least one fiber bundle in a target region. The therapeutic information comprises information regarding a stimulation preferability of the at least one fiber bundle. The calculation of the optimal position and orientation for implantation of the probe is based on the position, the orientation and the stimulation preferability of the at least one fiber bundle in the target region. At the optimal position and orientation, the probe is capable of generating an electric field gradient substantially parallel to at least one fiber bundle with a high stimulation preferability and/or substantially perpendicular to at least one fiber bundle with a low stimulation preferability.

According to a further aspect of the invention, a computer program product is provided for causing a processor to perform the above described method. These and other aspects of the invention are apparent from and will be elucidated with reference to the embodiments described hereinafter.

DETAILED DESCRIPTION OF THE INVENTION

Figure 1:
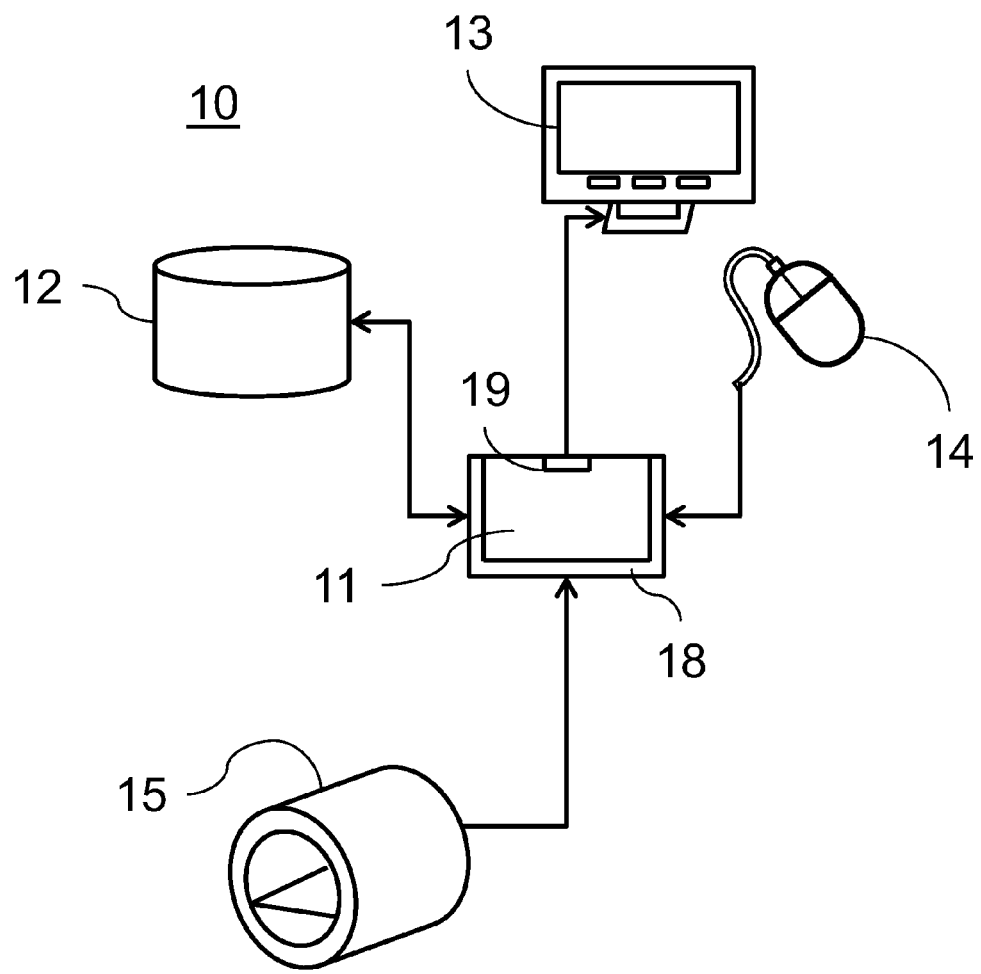
FIG. 1 schematically shows a planning system according to the invention.

FIG. 1 schematically shows a planning system 10 according to the invention. The planning system 10 may be embodied by a suitably programmed personal computer or by a dedicated medical system. The planning system 10 at least comprises an input 18 for receiving anatomical and therapeutic information and an optimization module for calculating the optimal position and orientation for implantation of the probe. The optimization module may be implemented in software, running on a processor 11. The system 10 preferably comprises, or is coupled to, a user interface for allowing the user to control the planning process. The user interface may comprise a keyboard and/or a pointing device, such as a mouse 14 for interacting with a graphical user interface displayed on a display 13. The display 13 is also coupled to the processor 11 via an output 19. A storage medium 12 is also coupled to the processor 11 and may, e.g., be used for storing program code, configuration data, medical information databases or patient data. The storage medium 12 may also comprise the anatomical data and therapeutic data that are needed for planning the implantation of the probe.

The system 10 may comprise or be coupled to an imaging apparatus 15 for obtaining images of the target region. Those images may be used for determining a position and an orientation of at least one fiber bundle in the target region. Usually Diffuse Tensor Imaging (DTI) is used for visualizing fiber bundles, but other imaging techniques may also be suitable for the planning method according to the invention. The processor 11 may be configured to derive positions and orientations of fiber bundles from the images. If no imaging apparatus 15 is used, the system 10 may, e.g., receive at the input 18 a list or database with position and orientation data of fiber bundles in the target region. Below, with reference to FIG. 2 it is elucidated how the system 10 is used for calculating the optimal position and orientation for implantation of the probe.

Figure 2:
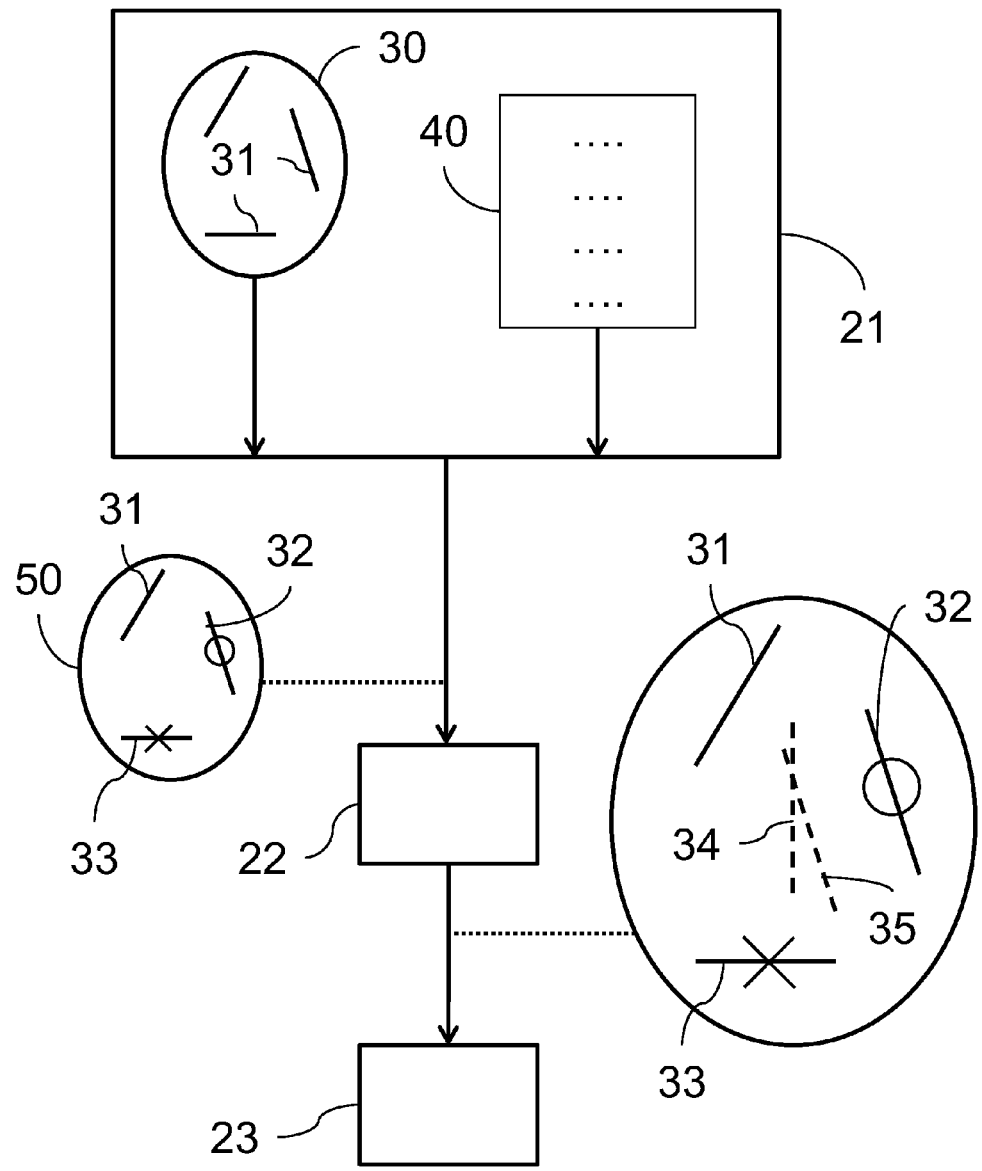
FIG. 2 shows a flow diagram of a method according to the invention.

FIG. 2 shows a flow diagram of a method according to the invention. The method starts with input step 21. The system 10 receives anatomical information 30 and therapeutic information 40. The anatomical information 30 may be in the form of an image of fiber bundles 31 in a target region, or may just be data describing fiber bundle positions and orientations. If the anatomical information 30 is provided in the form of images, the fiber bundle positions and orientations may be determined by dedicated image recognition software. The anatomical information 30 may cover, e.g., a larger brain region, allowing a user to select a target region. Selecting the target region may, e.g., be done using the pointing device 14 to select part of a 2D or 3D graphical representation of the region for which anatomical information 30 is available.

The therapeutic information 40 comprises information regarding the stimulation preferability of specific fiber bundles 31. The therapeutic information 40 may be symptom related and derived from, e.g., a database with medical information. Alternatively, it may be possible for a user to indicate which fiber bundles 31 should be stimulated and which ones not. The stimulation preferability may be a binary value indicating 'stimulation' or 'no stimulation', but may also be a continuous or discrete value on a scale ranging from 'stimulation highly preferable' to 'absolutely no stimulation'. When the anatomical data 31 and the therapeutic data 40 are combined, the combined data 50 comprises a list or database with fiber bundles 31, with for each fiber bundle a position, an orientation and a stimulation preferability. It is to be noted that fiber bundles 30 are not straight lines of uniform thickness. The input data preferably describes the full trajectory of a fiber bundle 30. Different parts of the fiber bundles 30 may have different orientations or shapes. The stimulation preferability of a fiber bundle 30 may also vary along the fiber bundle 30. The stimulation of the fiber bundle 30 may depend on the diameter of the fiber bundle 30. In FIG. 2, the combined data is visualized by highlighting a fiber bundle 32 that should be stimulated and a fiber bundle 33 for which stimulation is preferably avoided. Such a visualization may also be provided on a display 13 of the system 10.

In optimization step 22, the combined data is used 50 for calculating an optimal position and orientation for one or more probes. At the optimal position and orientation of the probe, the therapeutic effect of the stimulation may be maximized (probe 35 in FIG. 2) or the adverse side effects of the stimulation therapy may be minimized (probe 34 in FIG. 2). In most cases the optimal position and orientation of the probe will provide a balance between maximizing expected positive effects and minimizing the expected adverse effects. Since fiber bundles 31 may have different orientations at different positions, the optimal probe position may be close to a section of a fiber bundle 32 to be stimulated, which section is perpendicular to a nearby fiber bundle 33 which should not be stimulated.

For optimal stimulation of a target fiber 32, the probe is placed close to the bundle 32 to be stimulated. If the probe is closer to the fiber, the electrical stimulation field can be less strong and the chance of adverse effects caused by stimulation of nearby fiber bundles is reduced. Fiber bundles tend to be narrower at the center than close to the ends. When the probe is used to stimulate the fiber bundle where the diameter is relatively small, a less strong electrical stimulation field is required.

If the probe to be implanted is a multi-electrode probe, the optimization step 22 may take into account the possible 3D electrical field distributions that can be generated after implantation. Due to constraints on the distribution of stimulation electrodes (e.g. the geometry of the probe, limitation on the number of probes that can safely be implanted) not all 3D configurations of stimulation fields can be constructed. The optimization step 22 may thus compare the possible 3D orientations for the stimulation field to the positions and orientations of fiber bundles that should (or should not) be stimulated.

In output step 23, the results of the optimization step 22 are provided. The optimal position and orientation may, e.g., be provided as a data file with information about the optimal position and orientation. Such a data file may be used as input in a system for monitoring the actual implantation of the probe or probes. Instead of the planning system 10 providing data files with optimal positions and orientations, the display 13 of the planning system 10 may show images of the target region complemented with a graphical representation of the probe to be implanted.

Additionally, tolerance ranges may be shown for indicating how accurate the probe must be placed. Preferably, the system is also configured to show an actual position of a real probe during implantation. This would allow a surgeon to compare the actual position and orientation of the probe to the calculated optimal probe position. This may, e.g., be realized by superimposing the calculated optimal position for the probe on real time images of the target region.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

I claim:

1. A system for planning implantation of a neurostimulation probe, the system comprising:
    an input for receiving anatomical data comprising information regarding a position and an orientation of at least one fiber bundle in a target region;
    an input for receiving therapeutic information comprising information regarding a stimulation preferability of the at least one fiber bundle;
    an optimization module for calculating at least one optimal position and at least one optimal orientation for implantation of the neurostimulation probe based on the position, the orientation and the stimulation preferability of the at least one fiber bundle at which optimal position and orientation the probe is capable of generating an electric field gradient substantially parallel to at least one fiber bundle with a high stimulation preferability and/or substantially perpendicular to at least one fiber bundle with a low stimulation preferability; and
    an output for providing the optimal position and orientation.

2. A system for planning implantation of a neurostimulation probe according to claim 1, wherein the neurostimulation probe comprises an array of stimulation electrodes and the optimization module takes into account a range of 3D electrical field distributions that can be generated by the array of stimulation electrodes.

3. A system for planning implantation of a neurostimulation probe according to claim 1, further comprising a user interface for enabling a user to select the target region and/or the at least one fiber bundle with a high stimulation preferability and/or the at least one fiber bundle with a low stimulation preferability.

4. A system for planning implantation of a neurostimulation probe according to claim 1, wherein the output comprises a display for displaying a graphical representation of the target region and of the optimal position and orientation for implantation of the neurostimulation probe.

5. A system for planning implantation of a neurostimulation probe according to claim 1, further comprising a magnetic resonance imaging device for obtaining the anatomical data.

6. A method of planning implantation of a neurostimulation probe, the method comprising the steps of:
    receiving anatomical data comprising information regarding a position and an orientation of at least one fiber bundle in a target region;
    receiving therapeutic information comprising information regarding a stimulation preferability of the at least one fiber bundle;
    based on the position, the orientation and the stimulation preferability, calculating at least one optimal position and at least one optimal orientation for implantation of the neurostimulation probe at which optimal position and orientation the probe is capable of generating an electric field gradient substantially parallel to at least one fiber bundle with a high stimulation preferability and/or substantially perpendicular to at least one fiber bundle with a low stimulation preferability; and
    providing the optimal position and orientation.

7. A non-transitory computer program product for planning implantation of a neurostimulation probe, wherein the program is operative to cause a processor to perform the method as claimed in claim 6.

* * * * *